United States Patent
Haugaard et al.

(10) Patent No.: US 6,191,175 B1
(45) Date of Patent: Feb. 20, 2001

(54) PROCESS FOR THE SYNTHESIS OF A METHANOL/DIMETHYL ETHER MIXTURE FROM SYNTHESIS GAS

(75) Inventors: Jesper Haugaard, Lyngby; Bodil Voss, Virum, both of (DK)

(73) Assignee: Haldor Topsoe A/S, Lyngby (DK)

(*) Notice: Under 35 U.S.C. 154(b), the term of this patent shall be extended for 0 days.

(21) Appl. No.: 09/491,208

(22) Filed: Jan. 25, 2000

(30) Foreign Application Priority Data

Feb. 2, 1999 (DK) .............................. 1999 00132

(51) Int. Cl.⁷ .................................. C07C 27/00
(52) U.S. Cl. ................. 518/705; 518/700; 518/707; 518/713
(58) Field of Search ................... 518/700, 705, 518/707, 713

(56) References Cited

U.S. PATENT DOCUMENTS

| 4,098,809 | 7/1978 | Pagani ..................... 260/449 |
| 4,177,167 | 12/1979 | Manara et al. .............. 252/455 |
| 4,375,424 | 3/1983 | Slaugh ...................... 252/463 |
| 4,417,000 | 11/1983 | Slaugh et al. ............... 518/713 |
| 4,857,667 | * 8/1989 | Harandi et al. .............. 585/403 |
| 5,037,511 | 8/1991 | Dornhagen et al. .......... 203/37 |
| 5,254,596 | 10/1993 | Irick, Jr. et al. ............. 518/728 |

FOREIGN PATENT DOCUMENTS

| 2362944 | 7/1974 | (DE) . |
| 2757788 | 6/1978 | (DE) . |
| 3201155 | 10/1982 | (DE) . |
| 3118620 | 11/1982 | (DE) . |
| 3220547 | 1/1983 | (DE) . |
| 291937 | 7/1991 | (DE) . |
| 0164156 | * 6/1984 | (EP) . |
| 164156 | 12/1985 | (EP) . |
| 409086 | 1/1991 | (EP) . |
| 2093365 | 9/1982 | (GB) . |
| 2097383 | 11/1982 | (GB) . |
| 2099327 | 12/1982 | (GB) . |
| 96/23755 | * 8/1996 | (WO) . |

* cited by examiner

Primary Examiner—Shailendra Kumar
Assistant Examiner—J. Parsa
(74) Attorney, Agent, or Firm—Ostrolenk, Faber, Gerb & Soffen, LLP

(57) ABSTRACT

An improved process for the production of a methanol and dimethyl ether mixture rich in DME from essentially stoichiometrically balanced synthesis gas by a novel combination of synthesis steps.

8 Claims, 2 Drawing Sheets

PROCESS FOR THE SYNTHESIS OF A METHANOL/DIMETHYL ETHER MIXTURE FROM SYNTHESIS GAS

The present invention relates to a process for the synthesis of methanol and dimethyl ether (DME) from an essentially stoichiometrically balanced synthesis gas comprising $H_2/CO/CO_2$.

A product mixture with a high DME to methanol ratio is preferred as a product richer in DME in most cases represents a higher product value.

The product with the ultimate DME to methanol ratio obtained is a pure DME product, which is at present mainly produced at a high cost by dehydration of methanol by use of a dehydration catalyst in a fixed bed reactor, and rectification of the product to recover a DME product with high purity as required by the aerosol industry.

In many aspects a DME/methanol raw product mixture rich in DME is sufficient and thus preferred to a pure DME product if obtained at a lower cost than by methanol dehydration. Several methods are described in the literature where DME is produced directly in combination with methanol by a combined synthesis from synthesis gas by use of a catalyst active in both the synthesis of methanol from synthesis gas and methanol dehydration (DD Patent No. 291,937, EP Patent Nos. 164,156 and EP 409,086, GB Patent Nos. GB 2,093,365, GB 2,097,383 and GB 2,099,327, U.S. Pat. Nos. 4,417,000, 5,254,596, 4,177,167, 4,375,424 and 4,098,809, DE Patent Nos. 3,220,547, DE 3,201,155, DE 3,118,620, DE 2,757,788 and DE 2,362,944 and DK Patent Nos. 6031/87 and DK 2169/89).

Suitable catalysts for the use in the synthesis gas conversion stage include conventional employed methanol catalysts such as copper and/or zinc and/or chromium based catalysts and methanol dehydration catalysts, which usually comprise alumina or alumina silicates as active compounds arranged in a physical mixture or layered beds as cited in WO 96/23755.

The combined synthesis of methanol and DME from synthesis gas is conducted according to the following reaction schemes (all equilibrium reaction steps being exothermic, meaning heat is evolved, when displaced to the right hand side):

  (1)

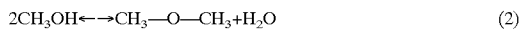  (2)

  (3)

Reaction schemes 1 and 3 are catalysed by catalysts active in methanol formation from synthesis gas, whereas reaction scheme 2 is catalysed by catalysts active in methanol dehydration. Combined catalysts, i.e. active in both methanol formation from synthesis gas and methanol dehydration thus catalyse all three reactions. The formation of the combined methanol (MeOH) and DME product is limited by chemical equilibrium. The equilibrium conversion of synthesis gas to the combined product increases with increasing pressure and decreasing reactor exit temperature.

Typical synthesis conditions are temperatures ranging from 200° C. to 310° C. and pressures in the range of 40–120 kg/cm².

Normally, unconverted synthesis gas is separated from the combined product downstream the synthesis reactor and recycled by means of a recycle compressor in order to obtain a higher overall conversion of the synthesis gas. The degree of separation of product from the recycled synthesis gas determines the equilibrium conversion per pass of synthesis gas. Methanol is substantially removed at moderate pressures by simple condensation at a temperature of the reactor effluent obtained at a low cost e.g. cooling by cooling water, whereas an efficient separation of DME from the synthesis gas requires either washing, cooling at lower temperature at substantially higher cost than obtained by cooling water, or condensation at high pressures or combinations thereof. Consequently, increasing the DME content in product results is increasing expenses to recover the DME/methanol product from the synthesis.

Increased deactivation of the catalyst sites active in methanol formation is observed at conditions with a high partial pressure of water, which makes restrictions for the application of catalysts with a methanol synthesis activity as to operating conditions.

The reactivity of the dehydration function of the combined catalyst increases more steeply with reaction temperature than does the methanol function, and at the same time the equilibrium conversion of dehydration is less sensitive to the temperature.

The methanol synthesis function is prone to deactivation at high temperature (e.g. more than 310° C.), whereas the dehydration function is far more resistant.

Likewise the composition of the synthesis gas decides for the obtainable conversion. Normally, when high conversions are desired a synthesis gas composition with a so-called module $$M = \frac{(n_{H_2} - n_{CO_2})}{(n_{CO} + n_{CO_2})}$$

About 2 is desired, as the components active in the reaction schemes are then stoichiometrically balanced. Compositions having modules of about the value 2 are essentially balanced, like typically module values between 1.8 and 2.2 are representing compositions considered essentially balanced.

Several compositions of synthesis gas meet the criterion. The higher the content of $CO_2$ in the synthesis gas, the lower is the equilibrium conversion.

The combined synthesis can be conducted in one or more fixed bed reactors loaded with the combined catalyst, it be cooled reactors, whereby reaction heat is removed from the reaction bed, or adiabatic type reactors typically placed in series with intercooling in a number providing for an appropriate conversion per pass. At high production capacities, it is found that adiabatic reactors are preferred to cooled reactors due to a favourable scale of economy. Typically, for obtaining a high conversion, three adiabatic reactors with two intercoolers in between are used.

It has now been found that a novel combination of process steps provides for an improved synthesis than the direct synthesis described above based on an essentially stoichiometrically balanced gas; the novel combination of process steps comprising Mixing make-up synthesis gas with unconverted recycle synthesis gas;

Heating the admixed synthesis gas to a predetermined methanol reactor inlet temperature; Optionally splitting a part of the preheated admixed synthesis gas;

Converting the remaining admixed preheated synthesis gas in a cooled reactor loaded with catalyst active in the synthesis of methanol from synthesis gas forming a cooled reactor effluent comprising methanol, water and unconverted synthesis gas;

optionally adding the split stream to the cooled reactor effluent;

passing the cooled reactor effluent to one or more beds of catalyst optionally comprising methanol synthesis function and/or combined catalyst function converting the synthesis gas further to DME, and a dehydration function converting the methanol further to DME, forming a DME reactor effluent;

cooling the DME reactor effluent;

separating the cooled DME reactor effluent into a stream mainly comprising unconverted synthesis gas, secondly comprising inert and reduced amounts of methanol and DME, and a stream mainly comprising the combined methanol and DME product and water;

splitting a purge stream from the said stream mainly comprising unconverted synthesis gas; and passing the remaining stream mainly comprising unconverted gas to a compressor raising the pressure of the stream to at least the pressure of the make-up synthesis gas providing a stream of unconverted recycle synthesis gas.

The catalysts active in methanol formation from synthesis gas may be selected from conventional employed methanol catalysts such as copper and/or zinc and/or chromium based catalysts, and the catalyst active in methanol dehydration may be selected from conventional employed methanol dehydration catalysts such as alumina or alumina silicates.

The advantages obtained when applying the technical features of the invention as presented above are that the combined synthesis step is split into at least two optimized steps:

Firstly, a pure methanol conversion, which accounts for the major conversion of synthesis gas, at conditions where the water from the dehydration of the methanol is eliminated, thus serving for a lower deactivation rate of the methanol synthesis activity;

Optionally secondly, a methanol synthesis or a combined synthesis for pushing the conversion of the methanol synthesis from synthesis gas further, at a higher temperature and where methanol is present in the cooled reactor effluent in a relatively high concentration, thus where the dehydration function of the combined catalyst is more active; and Thirdly, a reaction step where further solely dehydration of methanol takes place at further elevated temperature, thus where no shift activity converts water from the dehydration reaction with CO to $CO_2$, improving the quality of the unconverted synthesis gas for the purpose of recycle, however further raising the desired DME content of the DME reactor effluent.

A further advantage of the layout of the present invention is that the synthesis can be conducted at a higher pressure than when applying the combined direct synthesis at maintained methanol function deactivation rate as a lower water concentration is present in the methanol function catalysts. A high synthesis pressure also facilitates the removal of DME product from the unconverted synthesis gas. The layout in the present invention, among other parameters improved by the higher synthesis pressure level, serves for a high conversion per pass, meaning that the amount of recycled synthesis gas can be reduced at maintained overall conversion of synthesis gas. This again leads to the even further advantage than at maintained concentration of product in the recycle gas, the concentration of product in the synthesis gas admixture fed to the methanol synthesis reactor is reduced, further serving for an even higher possible conversion or alternatively a lower degree of separation of DME from the unconverted gas can be made, reducing the cost of DME product removal.

The lower recycle rate of unconverted synthesis gas reduces the size of the recycle compressor and the power consumption.

The bypass optionally installed around the cooled methanol synthesis reactor is controlling the approach to equilibrium for the methanol and shift reactions in the gas to the inlet of the subsequent methanol catalyst or combined catalyst bed, again utilized to control the outlet temperature from the combined catalyst bed.

An advantage of the bypass is that an intercooler/heater for temperature control can be eliminated, while at the same time controlling the methanol synthesis conversion from synthesis gas. The elimination of the need of further temperature adjustment between the second and third process reaction steps makes possible the placement of second and third bed within the same adiabatic reactor, reducing the cost of synthesis reactors compared to the combined direct synthesis.

These two embodiments of the present invention are described below and compared to a layout representing the direct combined synthesis.

EXAMPLE 1

Figure 1:
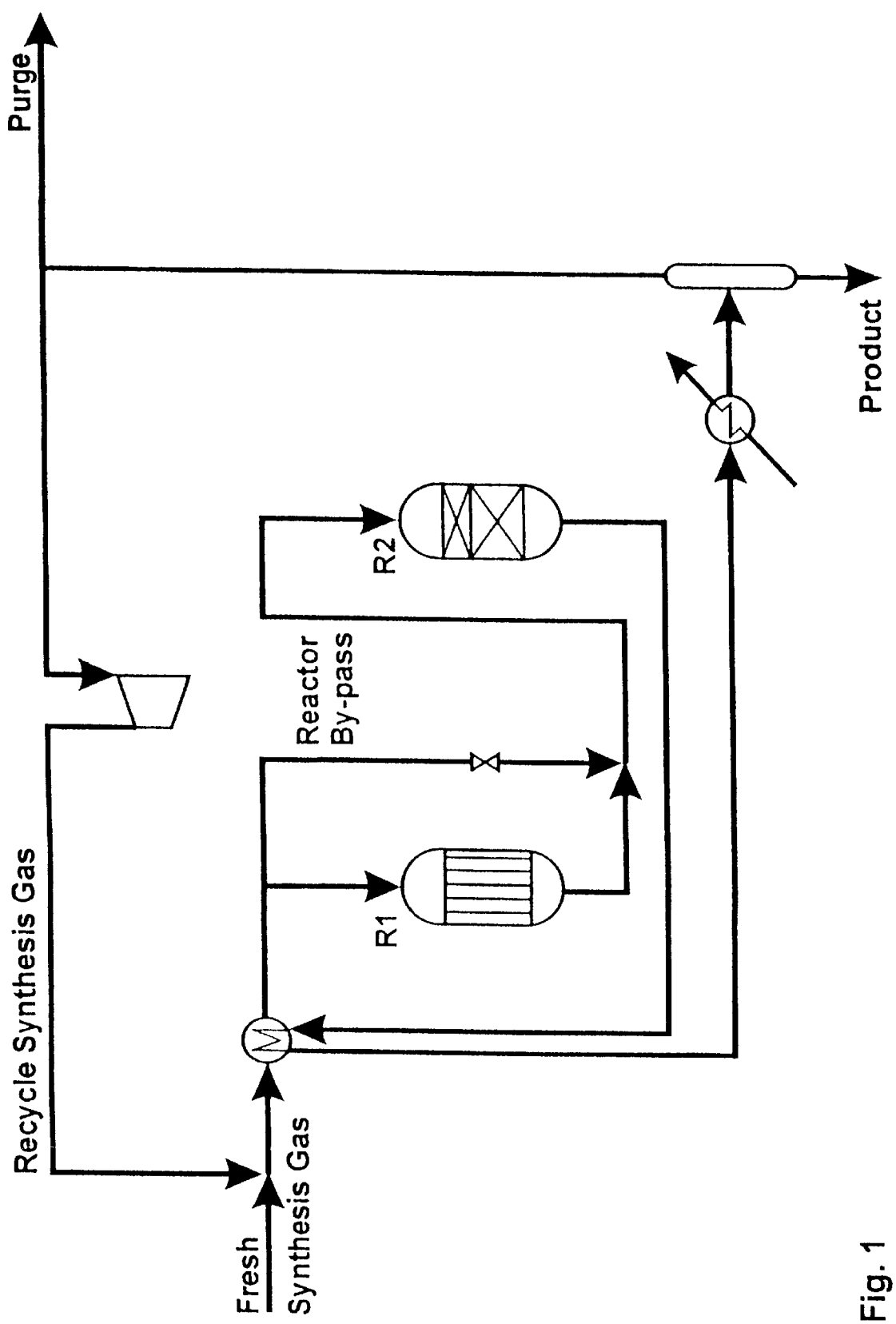
FIG. 1 diagrammatically illustrates a process according to this invention.

Reference is made to FIG. 1. This is a calculation example of the present invention.

The synthesis gas module as defined above is 2.05. The synthesis pressure is 107 kg/cm$^2$.

Fresh (make-up) synthesis gas is mixed with recycle synthesis gas and preheated to 225° C. A reactor by-pass stream (15%) is split from the reactor feed stream, before it is introduced to a cooled reactor (R1) loaded with a catalyst active in methanol synthesis. The cooled reactor is a boiling water reactor type with catalyst inside tubes is cooled on the shell side by boiling water, which serves to remove reaction heat. The pressure of the boiling water and thereby also its temperature (265° C.) controls the temperature of the cooled reactor effluent (274° C.). The by-pass stream is added to the cooled reactor effluent and passed to an adiabatic reactor (R2) containing a bed of combined catalyst and a bed of dehydration catalyst. The amount of bypass determines the temperature of the admixture (266° C.) and the temperature rise (21° C.) in the subsequent adiabatic bed of combined catalyst, thereby controlling the inlet temperature (287° C.) to the dehydration catalyst bed. The DME reactor effluent is cooled by heat exchange with the synthesis gas admixture and further by one or more coolers, eventually being cooled by typically cooling water to 35° C.

Product is separated from the unconverted synthesis gas, which is split into a purge gas stream and a recycle synthesis gas containing stream, which after repressurization in a recycle compressor is mixed with the fresh synthesis gas (as mentioned) for further conversion.

Results from the process calculation are presented in Tables 1 and 2 below.

The specific embodiment presented in the Example 1 above illustrated in FIG. 1 is one version of the invention which leads to an improved synthesis of DME and methanol from synthesis gas, however, other variations could be put up according to the basic features of the present invention, therefore, FIG. 1 should not be construed to limit the scope of the inventions or claims.

EXAMPLE 2

Figure 2:
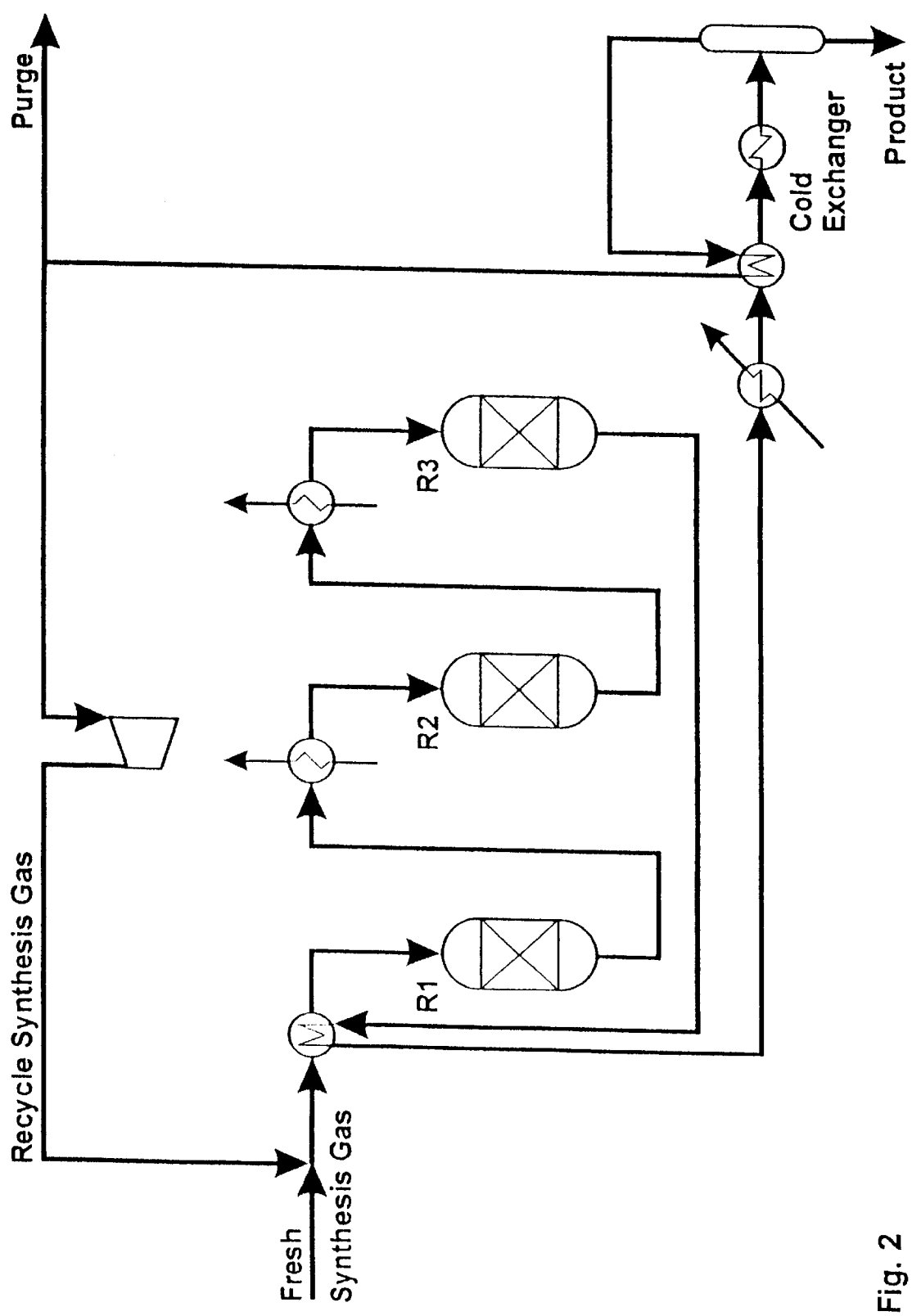
FIG. 2 diagrammatically illustrates a different embodiment according to this invention.

Reference is made to FIG. 2. This is not a calculation example of the present invention, but a comparative calculation example demonstrating one typical version of the layout of the direct DME synthesis.

The synthesis gas composition is identical to Example 1. The synthesis pressure is reduced to 80 kg/cm$^2$, as the water partial pressure formed under the combined synthesis would otherwise drastically deactivate the methanol function of the combined catalyst. This is also the reason for having to change the main conversion reactor type from a cooled to an adiabatic type, as the recycle rate in a cooled reactor layout is substantially lower.

All reactors (R1, R2, and R3) are loaded with combined catalyst as described above.

Fresh (make-up) synthesis gas is mixed with recycle synthesis gas and preheated to 231° C. and led to the first adiabatic conversion step (R1). The first reactor effluent reaches a temperature of 305° C. is then cooled to 245° C. in a reactor intercooler and led to the next adiabatic conversion step (R2). The effluent from the second reactor passes another intercooler and another conversion step (R3), why it is cooled by heat exchange with the cold synthesis gas admixture and one or more other heat exchangers. It is then cooled further in a so called cold exchanger, then further in a chiller to 0° C. and led to a separator, where unconverted synthesis gas is separated from synthesis products. The chilled gas is heated up in the cold exchanger, a purge gas stream is split from the synthesis gas before it is repressurized in a recycle compressor and mixed with fresh synthesis gas.

EXAMPLE 3

Reference is made to FIG. 1. In this calculation example of the present invention, the catalyst loaded into the second reactor (R2) is without the activity in methanol synthesis from synthesis gas as in Example 1, and thus representing another specific embodiment than Example 1. The bypass split around the cooled reactor (R1) is 0%.

The synthesis gas composition and pressure are identical to that of Example 1.

Fresh (make-up) synthesis gas is mixed with recycle synthesis gas and preheated to 225° C. The gas admixture is introduced to a cooled reactor (R1) loaded with a catalyst active in methanol synthesis. The cooled reactor is similar to that of Example 1, with boiling water at 265° C. The reactor effluent (273° C.) rich in methanol is passed on to a reactor (R2) loaded with dehydration catalyst, where methanol is converted to DME and water. The DME reactor effluent (305° C.) is cooled by heat exchange with the synthesis gas admixture and further by one or more coolers, eventually being cooled by typically cooling water to 35° C. As in Example 1, product is separated from the unconverted synthesis gas, which is split into a purge gas stream and a recycle stream, which after repressurisation in a recycle compressor is mixed with the fresh synthesis gas for further conversion.

Results from the process calculation are presented in Tables 1 and 2 below.

TABLE 1

Compositions from the synthesis comparison.

| | Flow sheet Positons | | | | | | | | |
|---|---|---|---|---|---|---|---|---|---|
| | Make-up Synthesis gas | | | Methanol Function Effluent | | | Condensate | | |
| | Example No. | | | | | | | | |
| | 1 | 2 | 3 | 1 | 2 | 3 | 1 | 2 | 3 |
| Components (mole %): | | | | | | | | | |
| $H_2$ | 66.24 | | | 50.30 | 58.18 | 51.78 | 0.55 | 0.47 | 0.60 |
| CO | 24.65 | | | 7.08 | 4.66 | 5.78 | 0.15 | 0.10 | 0.10 |
| $CO_2$ | 5.15 | | | 6.79 | 7.40 | 7.66 | 2.20 | 4.41 | 2.90 |
| Inerts | 3.77 | | | 18.02 | 18.78 | 17.16 | 0.74 | 0.61 | 0.59 |
| MeOH | | | | 8.38 | 2.13 | 8.04 | 29.60 | 28.88 | 30.15 |
| DME | | | | 8.04 | 6.03 | 7.71 | 24.38 | 26.87 | 24.78 |
| $H_2O$ | 0.18 | | | 1.39 | 2.82 | 1.87 | 42.38 | 38.66 | 40.88 |

The methanol function effluent is the composition of the synthesis gas in the position, where it leaves the last bed which contains catalyst active in methanol synthesis from synthesis gas, i.e. in Example 1 the first bed of the second reactor R2, in Example 2 the third reactor R3, and in Example 3 the first reactor R1. This composition has been presented as to demonstrate the maximum water concentration the methanol function catalyst is subjected to in the respective synthesis examples.

TABLE 2

| | Feed/ Production Index | Recycle/ Make-up Synthesis gas Ratio | Total molar Product Ratio* (DME/MeOH) | Catalyst Volume Index |
|---|---|---|---|---|
| Ex. 1 | 100/100 | 2.58 | 1.02 | 100 |
| Ex. 2 | 100/100 | 3.60 | 1.02 | 121 |
| Ex. 3 | 100/100 | 2.65 | 1.02 | 110 |

*) Incl. Products easily and cheaply obtained from purge gas stream.
Note: A larger amount of DME is recovered from the purge stream in Examples 1 and 3.

As it appears from the key figures in the above tables 1 and 2, a product mixture equally rich in DME is obtained in the calculation examples 1 and 3 of the present invention at a lower recycle rate with a lower amount of catalyst, and bearing in mind also that the Dme/methanol product is recovered at a low cost in Examples 1 and 3, and that the investment of equipment is reduced compared to Example 2, it is demonstrated that substantial improvements are gained when applying the process according to the present invention compared to the known combined direct synthesis.

What is claimed is:

1. A process for the production of a DME/methanol product mixture rich in DME from a make-up stream of an essentially stoichiometrically balanced synthesis gas comprising $H_2/CO/CO_2$, comprising the process steps of:

(a) splitting a bypass stream from the synthesis gas stream prior to passing the synthesis gas stream through a cooled reactor containing a catalyst active in methanol formation from synthesis gas, forming an effluent stream enriched in methanol and admixing with the said bypass stream;

(b) bringing the admixed stream from step (a) in contact with a catalyst active in methanol formation or active in both methanol formation and dehydration of methanol, forming a synthesis gas stream further enriched in methanol or DME;

(c) bringing the gas stream further enriched in methanol or DME from step (b) in contact with a catalyst active in dehydration of methanol, forming a synthesis gas stream further enriched in DME;

(d) withdrawing the synthesis gas stream enriched in DME from step (c) and separating the stream into a DME/methanol product mixture rich in DME and a synthesis gas containing stream; and (e) recycling a portion of the synthesis gas containing stream to the make-up stream of synthesis gas, forming the synthesis gas stream of step (a).

2. A process according to claim 1, wherein the catalysts in process steps (bb) and (b) are contained in a common reactor shell.

3. A process according to claim 1, wherein the process steps (bb) and (b) are performed in adiabatic manner.

4. A process according to claim 1, wherein the catalysts in process steps (b) and c are contained in a common reactor shell.

5. A process according to claim 1, wherein the process steps (b) and c are performed in adiabatic manner.

6. A process according to claim 1, wherein a bypass stream is split from the synthesis gas stream prior to passing it through the cooled reactor in step (a) and combining the bypass stream with the synthesis gas enriched in methanol prior to contacting it with the catalyst in step c.

7. A process according to claim 2, wherein a bypass stream is split from the synthesis gas stream prior to passing it through the cooled reactor in step (a) and combining the bypass stream with the synthesis gas enriched in methanol prior to contacting it with the catalyst in step c.

8. A process according to claim 3, wherein a bypass stream is split from the synthesis gas stream prior to passing it through the cooled reactor in step (a) and combining the bypass stream with the synthesis gas enriched in methanol prior to contacting it with the catalyst in step c.

* * * * *